(12) United States Patent
Ishiyama (10) Patent No.: US 10,729,401 B2
(45) Date of Patent: Aug. 4, 2020

(54) HIGH-VOLTAGE DEVICE AND MEDICAL-IMAGE DIAGNOSTIC APPARATUS

(71) Applicant: Toshiba Medical Systems Corporation, Otawara-shi, Tochigi (JP)

(72) Inventor: Fumio Ishiyama, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 154 days.

(21) Appl. No.: 15/810,196

(22) Filed: Nov. 13, 2017

(65) Prior Publication Data
US 2018/0153500 A1 Jun. 7, 2018

(30) Foreign Application Priority Data
Dec. 5, 2016 (JP) .................................. 2016-235987

(51) Int. Cl.
| | | |
|---|---|---|
| A61B 6/00 | (2006.01) | |
| A61B 6/03 | (2006.01) | |
| H05G 1/32 | (2006.01) | |
| H01F 27/40 | (2006.01) | |
| H01F 27/32 | (2006.01) | |

(Continued)

(52) U.S. Cl.
CPC .............. *A61B 6/56* (2013.01); *A61B 6/032* (2013.01); *A61B 6/40* (2013.01); *A61B 6/484* (2013.01); *H01F 27/324* (2013.01); *H01F 27/40* (2013.01); *H01F 30/04* (2013.01); *H02M 7/106* (2013.01); *H05G 1/12* (2013.01); *H05G 1/32* (2013.01)

(58) Field of Classification Search
None
See application file for complete search history.

(56) References Cited

U.S. PATENT DOCUMENTS

| | | | |
|---|---|---|---|
| 5,363,286 A | 11/1994 | Tsuchiya | |
| 2014/0268968 A1* | 9/2014 | Richardson | H01F 27/42 363/140 |

(Continued)

FOREIGN PATENT DOCUMENTS

| | | |
|---|---|---|
| JP | 05-176540 | 7/1993 |
| JP | H07-320892 A | 12/1995 |

(Continued)

OTHER PUBLICATIONS

Japanese Office Action dated Jun. 2, 2020, issued in Japanese Patent Application No. 2016-235987.

*Primary Examiner* — Hoon K Song
(74) *Attorney, Agent, or Firm* — Oblon, McClelland, Maier & Neustadt, L.L.P.

(57) ABSTRACT

A high-voltage device according to embodiments comprises an inverter circuit configured to convert a direct-current voltage into an alternating-current voltage, a high-voltage transformer, an insulating layer and a conductive layer. The high-voltage transformer includes a primary coil on an input side and multiple secondary coils on an output side and raises a voltage of output of the inverter circuit. The insulating layer is provided on an outer circumference of a bundle of winding wires of each of the secondary coils so as to individually cover each of the secondary coils. The conductive layer is provided on an outer circumference of each of the insulating layers so as to individually cover each of the insulating layers.

9 Claims, 8 Drawing Sheets

(51) Int. Cl.
*H05G 1/12* (2006.01)
*H01F 30/04* (2006.01)
*H02M 7/10* (2006.01)

(56) References Cited

U.S. PATENT DOCUMENTS

2016/0286636 A1* 9/2016 Ogawa .................... H05G 1/32
2018/0205356 A1* 7/2018 Hirata ................. B60R 16/0207

FOREIGN PATENT DOCUMENTS

| | | |
|---|---|---|
| JP | 2005-032829 A | 2/2005 |
| JP | 2005-150264 A | 6/2005 |
| JP | 2007-173010 A | 7/2007 |
| JP | 2012-195412 A | 10/2012 |
| JP | 5281444 | 9/2013 |
| JP | 2015-133353 A | 7/2015 |
| WO | WO 2015/079922 A1 | 6/2015 |

* cited by examiner

HIGH-VOLTAGE DEVICE AND MEDICAL-IMAGE DIAGNOSTIC APPARATUS

CROSS-REFERENCE TO RELATED APPLICATIONS

This application is based upon and claims the benefit of priority from Japanese Patent Application No. 2016-235987, filed on Dec. 5, 2016; the entire contents of which are incorporated herein by reference.

FIELD

Embodiments described herein relate generally to a high-voltage device and a medical-image diagnostic apparatus.

BACKGROUND

With regard to a high-voltage generator, which is one of the elements that constitute an X-ray high-voltage device, included in an X-ray CT apparatus or an X-ray diagnostic apparatus, in order to reduce the size or ensure the dielectric strength voltage, its contents are immersed in insulating oil or is hardened with insulating resin, or the like. Particularly, in X-ray CT apparatuses, as a high-voltage generator is placed on a rotary gantry, all or some of the components, included in the high-voltage generator, are often hardened with resin.

In this case, liquid resin is injected into the container that houses assembled and wired components and is then hardened. The resin injection operation is conducted in a vacuum, or a vacuum defoaming process is performed after resin is injected. This is intended for reduction of spaces, what are called voids, in which resin does not enter, as much as possible. If a void is present in the hardened resin, there is a possibility that the electric field is concentrated (corona discharge) at the void at the time of generation of a high voltage and insulation breakdown occurs. There is a problem in that, if an X-ray CT apparatus, an X-ray diagnostic apparatus, or the like, is used and insulation breakdown occurs in the middle of diagnosis, the apparatus gets damaged and the diagnosis is interrupted.

As secondary winding wires of a high-voltage transformer in a high-voltage generator are wound closely due to a small wire diameter, resin is unlikely to penetrate between the wires. Furthermore, as particulate or fiber-like material, called filler, is mixed to improve the dielectric strength voltage or the radiation performance of resin, it is further difficult to permeate resin between the secondary winding wires of the high-voltage transformer without generating voids.

Furthermore, the relative permittivity of the above-described resin is higher than that of vacuum, air, or insulating oil; therefore, if the secondary winding wires of the high-voltage transformer are hardened with resin, the distributed capacitance between the secondary winding wires is increased. As the wattless current flows into the distributed capacitance between the secondary winding wires, there is a problem in that the wattless current in an inverter circuit, which drives the high-voltage generator, is increased so that the efficiency of the X-ray high-voltage device is lowered and the inverter circuit or the high-voltage transformer gets overheated. Furthermore, as an increase in the distributed capacitance between the secondary winding wires causes a decrease in the resonance frequency of the high-voltage transformer, a rise in the operating frequency of the inverter circuit is constrained, and a reduction in the size of the high-voltage generator is interrupted.

DETAILED DESCRIPTION

A high-voltage device according to embodiments comprises an inverter circuit, a high-voltage transformer, an insulating layer and a conductive layer. The inverter circuit is configured to convert a direct-current voltage into an alternating-current voltage. The high-voltage transformer includes a primary coil on an input side and multiple secondary coils on an output side and raises a voltage of output of the inverter circuit. The insulating layer is provided on an outer circumference of a bundle of winding wires of each of the secondary coils so as to individually cover each of the secondary coils. The conductive layer is provided on an outer circumference of each of the insulating layers so as to individually cover each of the insulating layers.

With reference to the drawings, an explanation is given below of the high-voltage device and a high-voltage generator according to an embodiment. Furthermore, an X-ray high-voltage device 6 is explained below as an example of the high-voltage device. Moreover, high-voltage generators 71, 72 are explained below as examples of the high-voltage generator. In the following explanations, duplicated explanations are appropriately omitted.

Figure 1:
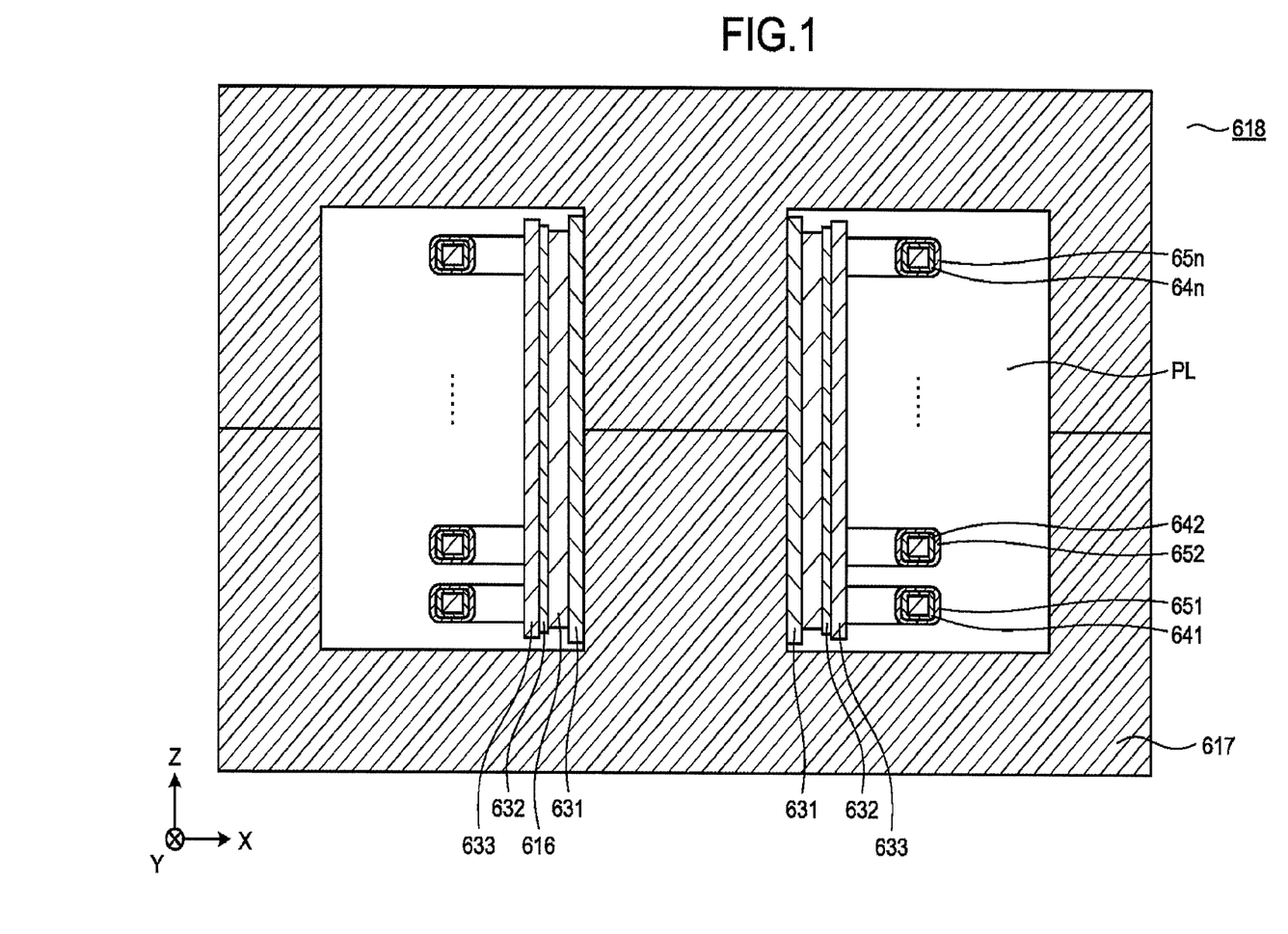
FIG. 1 is a cross-sectional view of a high-voltage transformer according to an embodiment.

With reference to FIG. 1, FIG. 2, FIG. 3, FIG. 4, FIG. 5, and FIG. 6, an explanation is given of the configurations of a high-voltage transformer 618 and high-voltage rectifying-smoothing circuits 6191 and 6192. FIG. 1 is a diagram that illustrates one of the high-voltage transformers 618 according to the embodiment, which is cross-sectioned on the plane parallel to the ZX plane as viewed in −Y direction. The high-voltage transformer 618 in FIG. 1 is a shell-type single-phase transformer, and a single primary coil 616 and n secondary coils I11 to I1n are coaxially wound around the center leg of a core 617. The core 617 in FIG. 1 is for example an EER-type ferrite core. The primary coil 616 is wound around a winding form 631 so as to be insulated from the core 617. The primary coil 616 is a coil on the input side, provided in the high-voltage transformer 618. An insulating film 632 and a shield plate 633 are provided on the primary coil 616. The n secondary coils I11 to I1*n* are covered with insulating layers 641 to 64*n*, and furthermore the outside of the insulating layers 641 to 64*n* are covered with conductive layers 651 to 65*n*. The secondary coils I11 to I1*n* are coils on the output side, provided in the high-voltage transformer 618.

Figure 2:
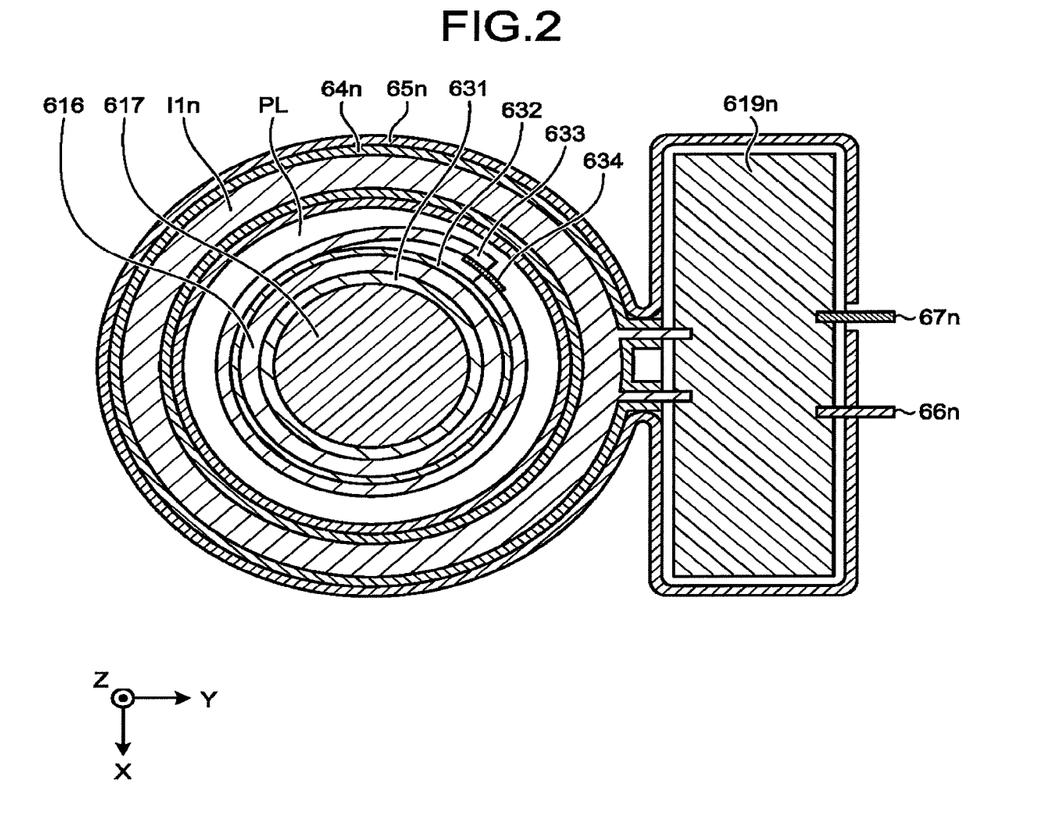
FIG. 2 is a cross-sectional view of the high-voltage transformer and a high-voltage rectifying-smoothing circuit according to the embodiment with respect to the XY plane.

FIG. 2 is a diagram of the high-voltage transformer 618 according to the embodiment and one of high-voltage rectifying-smoothing circuits 619*n*, connected to the high-voltage transformer 618, which is cross-sectioned on the plane parallel to the XY plane when the inner side area of the resin is viewed in +Z direction. Although I1*n* is explained as an example among the n secondary coils in FIG. 2, the secondary coils I11 to I1*n*-1 also have the same structure. The winding start and the winding end of the shield plate 633 are insulated with an insulating film 634 so that they are prevented from being shunted. The high-voltage rectifying-smoothing circuit 619*n* is connected to two terminals of the secondary coil I1*n* so that it rectifies and smooths the voltage, guided into the secondary coil I1*n*, and outputs direct-current voltage to terminals 66*n* and 67*n*. In the example illustrated in FIG. 2, the secondary coil I1*n* and the high-voltage rectifying-smoothing circuit 619*n* are integrated and covered with the conductive layer 65*n*; however, it is possible that the secondary coil I1*n* and the high-voltage rectifying-smoothing circuit 619*n* are separated and only the secondary coil I1*n* is covered with the conductive layer 65*n*.

Figure 3:
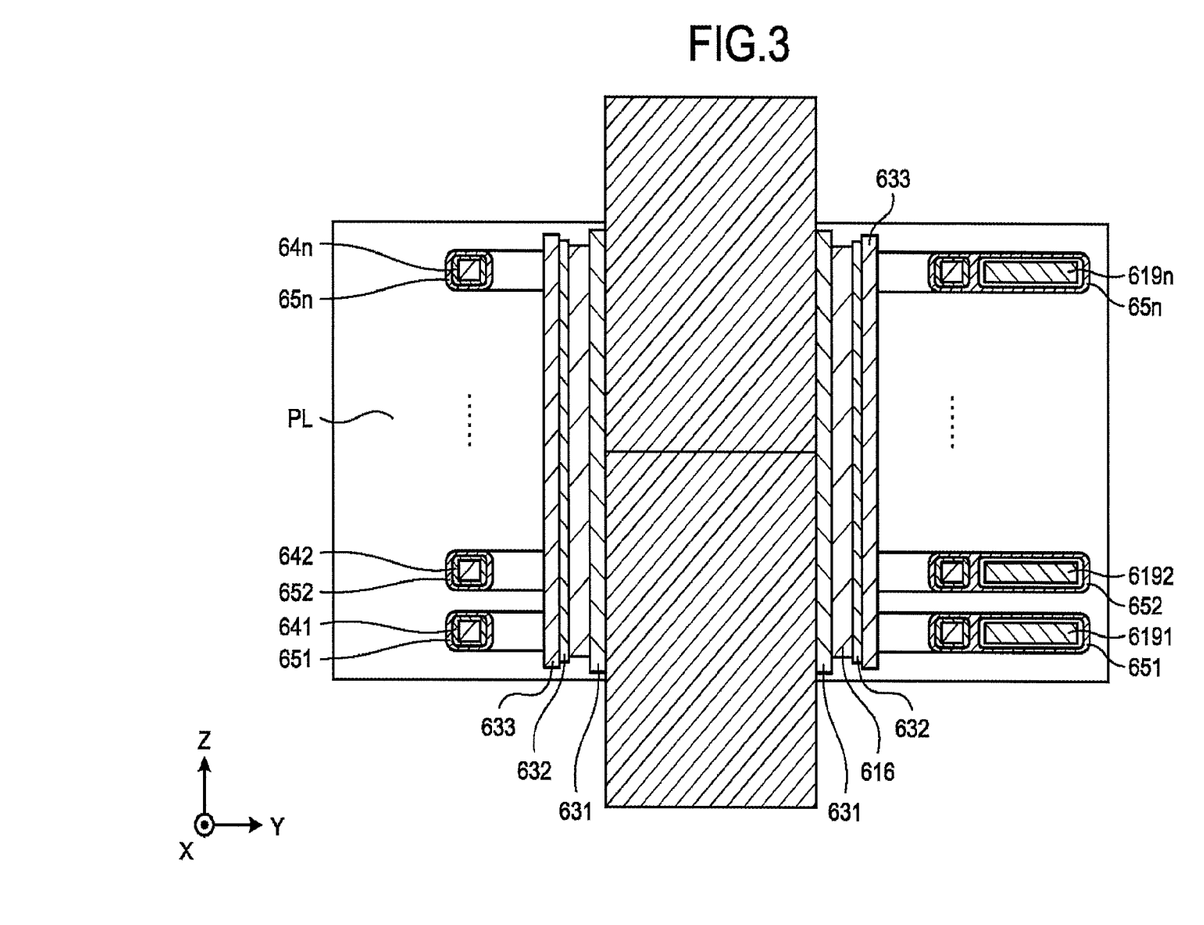
FIG. 3 is a cross-sectional view of the high-voltage transformer and the high-voltage rectifying-smoothing circuit according to the embodiment with respect to the plane.

FIG. 3 is a diagram of the high-voltage transformer 618 according to the embodiment and the high-voltage rectifying-smoothing circuits 6191 to 619*n* connected to the high-voltage transformer 618, which are cross-sectioned on the plane parallel to the YZ plane as viewed in +X direction. The output terminals of the high-voltage rectifying-smoothing circuits 6191 to 619*n* are cascade-connected, and a direct-current high voltage is output at both ends of them. The high-voltage rectifying-smoothing circuits 6191 to 619*n* may be configured by using Cockcroft-Walton circuits, voltage-doubler rectifying circuits, or full-wave rectifying circuits. The conductive layers 651 to 65*n* are covered with resin PL so as to be insulated from the core 617, the primary coil 616, and the shield plate 633.

As illustrated in FIG. 1, FIG. 2, and FIG. 3, the insulating layer 641 to the insulating layer 64*n* cover the secondary coil I11 to the secondary coil I1*n*, respectively. That is, the insulating layer 641 to the insulating layer 61*n* are containers that are made of insulating material and that house the secondary coil I11 to the secondary coil I1*n*, respectively. Alternatively, the insulating layer 641 to the insulating layer 64*n* are hollow members that are made of insulating material and that house the secondary coil I11 to the secondary coil I1*n*, respectively.

These insulating layers are formed by for example immersing a secondary coil in melted resin. Alternatively, these insulating layers are formed by attaching thermosetting resin powder to a secondary coil and heating it. Furthermore, if these methods are implemented in 1 atmosphere, depressurized atmosphere, or inert gas, air or inert gas may remain between winding wires of the secondary coil I11 to the secondary coil I1*n*.

Furthermore, the insulating layer 641 to the insulating layer 64*n* may cover the high-voltage rectifying-smoothing circuit 6191 to the high-voltage rectifying-smoothing circuit 619*n*, respectively, in addition to the secondary coil I11 to the secondary coil I1*n*. Moreover, the insulating layer 641 to the insulating layer 64*n* may cover the high-voltage rectifying-smoothing circuit 6191 to the high-voltage rectifying-smoothing circuit 619*n*, respectively, instead of the secondary coil I11 to the secondary coil I1*n*.

Furthermore, an insulating layer may be provided in at least one of the gaps between the conductive layer 651 and the high-voltage rectifying-smoothing circuit 6191, the conductive layer 6 and the high-voltage rectifying-smoothing circuit 2, and to the conductive layer 65*n* and the high-voltage rectifying-smoothing circuit 619*n*.

Figure 4:
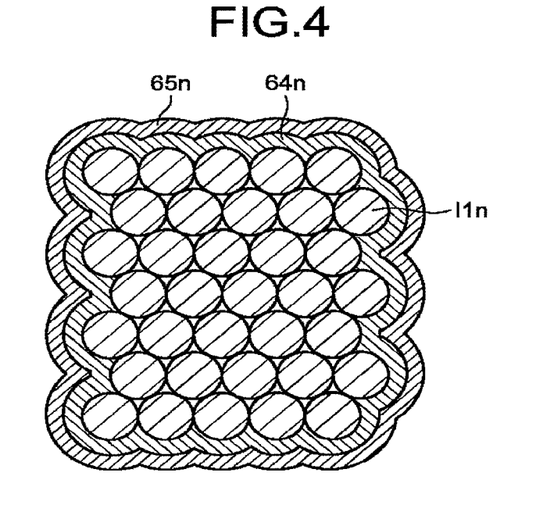
FIG. 4 is a diagram that illustrates a secondary coil, an insulating layer that covers it, and a conductive layer.
Figure 5:
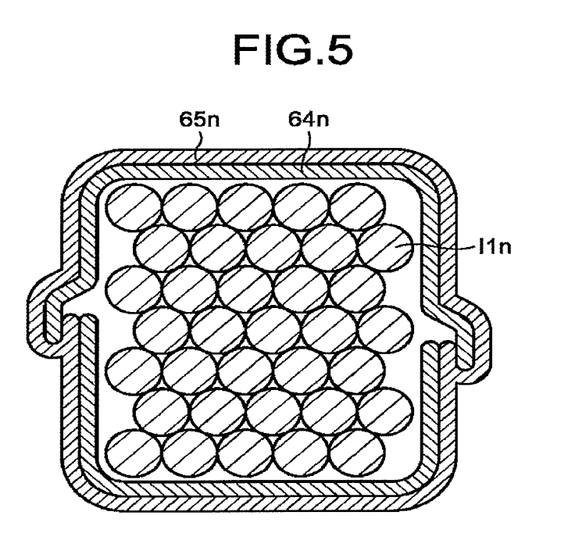
FIG. 5 is a diagram that illustrates another example of the secondary coil, the insulating layer that covers it, and the conductive layer.

As illustrated in FIG. 3, FIG. 4, and FIG. 5, the conductive layer 651 to the conductive layer 65*n* are conductive hollow members. The conductive layer 651 to the conductive layer 65*n* house the secondary coil I11 and the high-voltage rectifying-smoothing circuit 6191 to the secondary coil I1*n* and the high-voltage rectifying-smoothing circuit 619*n*, respectively. That is, as illustrated in FIG. 5, the conductive layer 651 to the conductive layer 65*n* are provided to cover the secondary coil I11 and the high-voltage rectifying-smoothing circuit 6191 to the secondary coil I1*n* and the high-voltage rectifying-smoothing circuit 619*n*, respectively. Furthermore, in other words, as illustrated in FIG. 5, the conductive layer 651 to the conductive layer 65*n* are provided to cover the entire surface of the secondary coil I11 and the high-voltage rectifying-smoothing circuit 6191 to the secondary coil I1*n* and the high-voltage rectifying-smoothing circuit 619*n*, respectively.

Furthermore, as illustrated in FIG. 3, FIG. 4, and FIG. 5, the conductive layer 651 to the conductive layer 65*n* house the insulating layer 641 to the insulating layer 64*n*, respectively. Specifically, as illustrated in FIG. 3, FIG. 4, and FIG. 5, the conductive layer 651 to the conductive layer 65*n* are provided to cover the insulating layer 641 to the insulating layer 64*n*, respectively. Furthermore, in other words, as illustrated in FIG. 3, FIG. 4, and FIG. 5, the conductive layer 651 to the conductive layer 65*n* are provided to cover the entire surface of the insulating layer 641 to the insulating layer 64*n*, respectively. That is, the conductive layer 651 and the conductive layer 652 to the conductive layer 65*n* are formed on the outside of the respective insulating layers.

Furthermore, the conductive layer 651 to the conductive layer 65*n* may include a hollow area to house the secondary coil I11 to the secondary coil I1*n*, respectively, and a hollow area to house the high-voltage rectifying-smoothing circuit 6191 to the high-voltage rectifying-smoothing circuit 619*n*, respectively.

Furthermore, the conductive layer 651 to the conductive layer 65*n* may house only the secondary coil I11 to the secondary coil I1*n*, respectively. That is, the conductive layer 651 to the conductive layer 65*n* may be provided to cover only the secondary coil I11 to the secondary coil I1*n*, respectively. Furthermore, in other words, the conductive layer 651 to the conductive layer 65*n* may be provided to cover the entire surface of only the secondary coil I11 to the secondary coil I1*n*, respectively. Alternatively, the conductive layer 651 to the conductive layer 65*n* may house only the high-voltage rectifying-smoothing circuit 6191 to the high-voltage rectifying-smoothing circuit 619*n*, respectively. That is, the conductive layer 651 to the conductive layer 65*n* may cover only the high-voltage rectifying-smoothing circuit 6191 to the high-voltage rectifying-smoothing circuit 619*n*, respectively.

Here, if the conductive layer 651 to the conductive layer 65*n* cover the high-voltage rectifying-smoothing circuit 6191 to the high-voltage rectifying-smoothing circuit 619*n*, respectively, the conductive layer 651 to the conductive layer 65n are electrically connected to a single point of the high-voltage rectifying-smoothing circuit 6191 to the high-voltage rectifying-smoothing circuit 619n, respectively.

Specifically, the conductive layer 651 to the conductive layer 65n are electrically connected to the terminals that are closer to the ground voltage among the output terminals of the high-voltage rectifying-smoothing circuit 6191 to the high-voltage rectifying-smoothing circuit 619n.

The conductive layer 651 to the conductive layer 65n only have to be conductive. Therefore, the conductive layer 651 to the conductive layer 65n are membranes that are made of resin in which, for example, metallic membranes or carbon is impregnated. Furthermore, the metallic membrane is formed by for example vapor deposition. Furthermore, membranes made of resin in which, carbon is impregnated, are formed by for example applying resin including carbon to each insulating layer.

As illustrated in FIG. 5, FIG. 4, and FIG. 5, the circumferences of the conductive layer 651 to the conductive layer 65n are filled with the resin PL.

FIG. 4 is an enlarged view of the secondary coil I1n, the insulating layer 64n that covers it, and the conductive layer 65n in FIG. 1. The insulating layer 64n, which is like a thin membrane, is provided outside the secondary coil I1n, and the conductive layer 65n, which is like a thin membrane, is further provided outside it. There is a void space between winding wires of the secondary coil I1n, and dry air or inert gas is present. As there is no resin between winding wires of the secondary coil I1n, inter-winding distributed capacitance may be reduced. In FIG. 4, self-fusing electric wires are used as the winding wires of the secondary coil I1n so that a bobbin is not necessary. As another method for implementing the insulating layer 64n and the conductive layer 65n, there is also a method by which the secondary coil I1n is housed in a thin resin case, the outside of which is subjected to conductive coating or conductive processing due to metal deposition, or the like, as in FIG. 5. Alternatively, there is also a method by which the secondary coil I1n is housed in a case that is made of resin that is conductive after being mixed with carbon, or the like. In this case, winding-wire covering of the secondary coil I1n forms an insulating layer. The resin case may also be used as a bobbin which the secondary coil I1n is wound around. Furthermore, the secondary coil I11 to the secondary coil I1n-1 also have the same structure.

Figure 6:
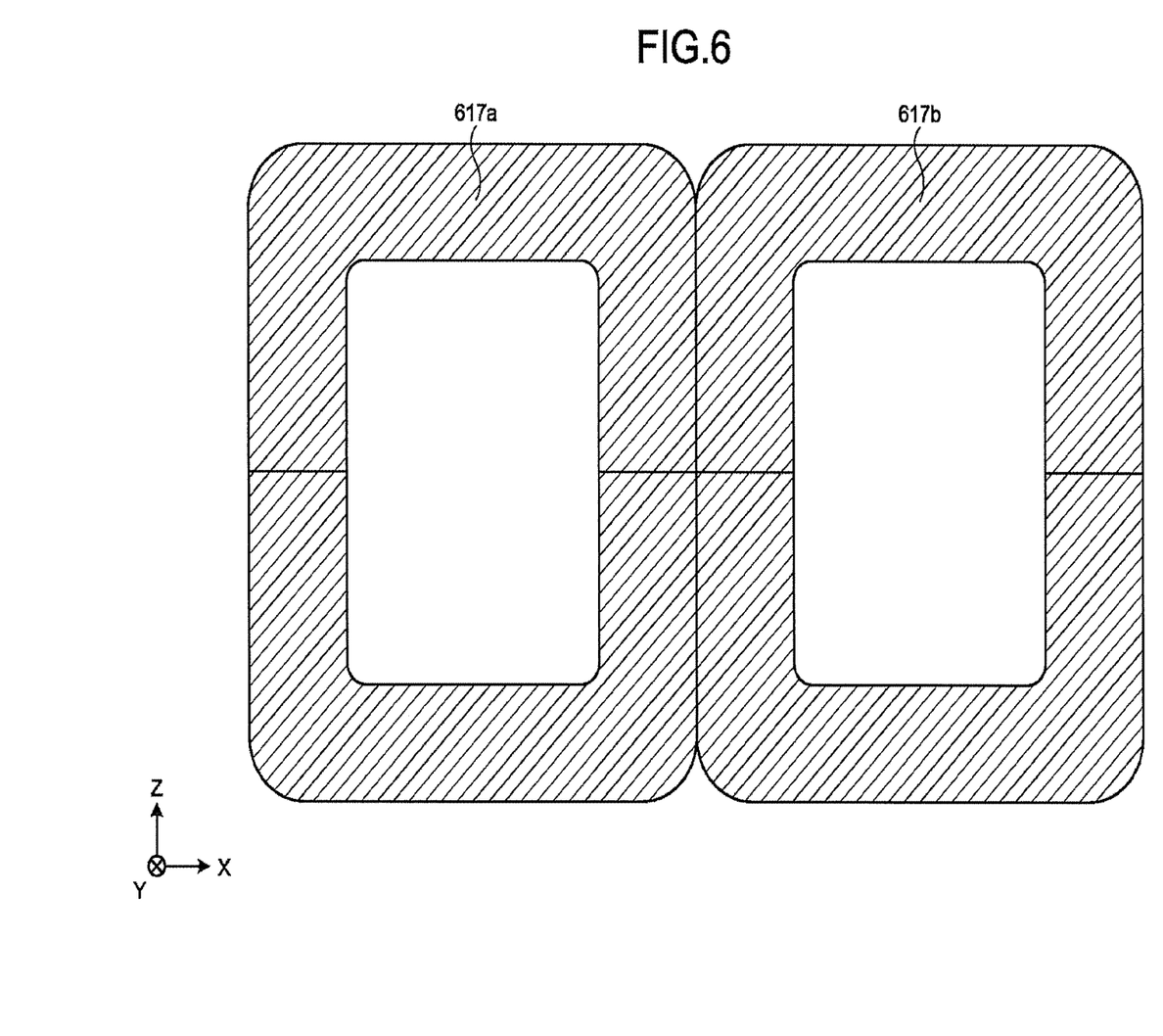
FIG. 6 is a diagram that illustrates another example of the configuration of a core that is included in the high-voltage transformer according to the embodiment.

FIG. 6 illustrates the core shape if the core made of, for example, silicon steel, oriented magnetic steel, amorphous magnetic material, or nanocrystalline magnetic material is used instead of the core 617 that is made of ferrite. In this case, U-U cores 617a and 617b form cores. They are also called cut cores as they are manufactured by being cut into two after a strip-shaped core material is wound around a form. If the cut core is used, the core cross-sectional surface is typically rectangular, and therefore the coil is sometimes wound in a rectangular shape.

Figure 7:
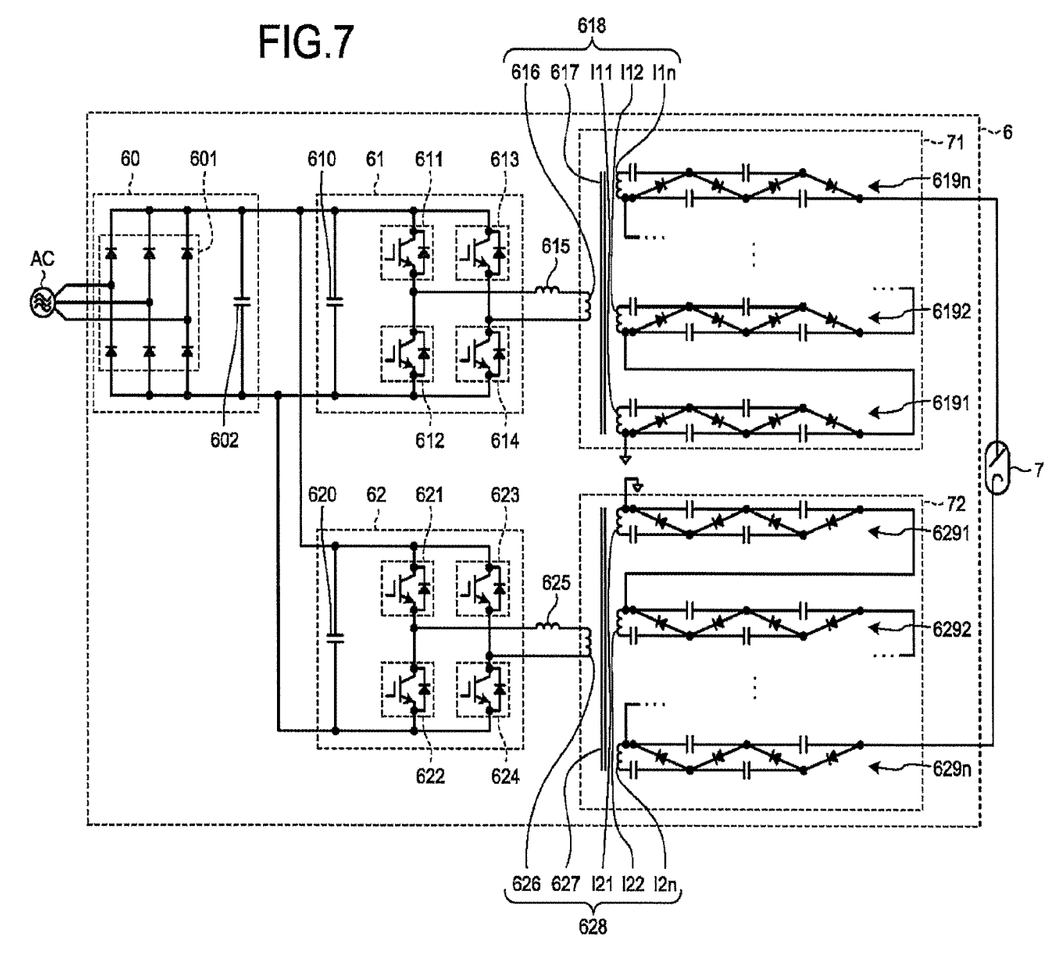
FIG. 7 is a diagram that illustrates an example of the circuit structure of the X-ray high-voltage device according to the embodiment.

With reference to FIG. 7, the circuit structure the X-ray high-voltage device 6 according to the embodiment is explained. As illustrated in FIG. 7, the X-ray high-voltage device 6 receives the voltage of the three-phase alternating-current power source AC as an input and supplies a positive direct-current high voltage and a negative direct-current high voltage to an X-ray tube 7. The X-ray tube 7 is a neutral-grounding type, and it applies a positive direct-current high voltage to the anode and a negative direct-current high voltage to the cathode.

The X-ray high-voltage device 6 include an AC/DC converter circuit 60, two inverter circuits 61, 62, two coils 615, 625, and the two high-voltage generators 71, 72. The AC/DC converter circuit 60 includes a three-phase rectifying diode bridge 601 and a smoothing capacitor 602. The inverter circuit 61 includes a rail capacitor 610 and switching elements 611 to 614. The switching elements 611 to 614 are controlled so as to be on/off by undepicted control circuitry so that they convert a direct-current voltage into an alternating-current voltage. The inverter circuit 62 includes a rail capacitor 620 and switching elements 621 to 624. The switching elements 621 to 624 are controlled so as to be on/off by undepicted control circuitry so that they convert a direct-current voltage into an alternating-current voltage. Specifically, the gates of the switching elements 611 to 624 are controlled so as to be on/off by undepicted control circuitry so that they convert a direct-current voltage into an alternating-current voltage. In the illustrated example, the switching elements 611 to 614 and the switching elements 621 to 624 are the inverse-parallel circuit of diodes and the Insulated Gate Bipolar Transistor (IGBT); however, instead of the IGBT, bipolar transistor, power MOSFET, Junction FET, or the like, may be used. The high-voltage generator 71 includes the high-voltage transformer 618 and the high-voltage rectifying-smoothing circuits 6191 to 619n. Similarly, the high-voltage generator 72 includes a high-voltage transformer 628 and high-voltage rectifying-smoothing circuits 6291 to 629n. The high-voltage transformer 628 is a shell-type single-phase transformer, and a single primary coil 626 and n secondary coils I21 to I2n are coaxially wound around the center leg of a core 627. The primary coil 626 is a coil on the input side, provided in the high-voltage transformer 628. The secondary coils I21 to I2n are coils on the output side, provided in the high-voltage transformer 628. Furthermore, the core 627 is an EER-type ferrite core. In the example illustrated in FIG. 7, the high-voltage rectifying-smoothing circuits 6191 to 619n and the high-voltage rectifying-smoothing circuits 6291 to 629n are two-stage Cockcroft-Walton circuit; however, a full-wave rectifying circuit or a voltage-doubler rectifying circuit may be used. The coil 615 is connected between the inverter circuit 61 and the high-voltage generator 71. Instead of the coil 615, leakage inductance of the high-voltage transformer 618 may be used. The coil 625 is connected between the inverter circuit 62 and the high-voltage generator 72. Instead of the coil 625, leakage inductance of the high-voltage transformer 628 may be used.

Each of the high-voltage rectifying-smoothing circuits 6191 to 619n in the high-voltage generator 71 outputs a positive direct-current voltage, and the outputs are cascade-connected. The minus output terminal of the high-voltage rectifying-smoothing circuit 6191 is grounded, and a positive direct-current high voltage is obtained at the plus output terminal of the high-voltage rectifying-smoothing circuit 619n. In the same manner, each of the high-voltage rectifying-smoothing circuits 6291 to 629n in the high-voltage generator 72 outputs a negative direct-current voltage, and the outputs are cascade-connected. The plus output terminal of the high-voltage rectifying-smoothing circuit 6291 is grounded, and a negative direct-current high voltage is obtained at the minus output terminal of the high-voltage rectifying-smoothing circuit 629n.

In FIG. 7, the high-voltage generator 71, which generates a positive high voltage, and the high-voltage generator 72, which generates a negative high voltage, are separated; however, they may be combined to be a single high-voltage generator.

If the inverter circuit 61 and the inverter circuit 62 are operated with a phase shift of 90°, ripple of the voltage applied to the X-ray tube 7 may be reduced. Furthermore, if the polarities of the secondary winding wires of the high-voltage transformer 618 and the high-voltage transformer 629 are alternately reversed, ripple of the voltage applied to the X-ray tube 7 may be further reduced.

Figure 8:
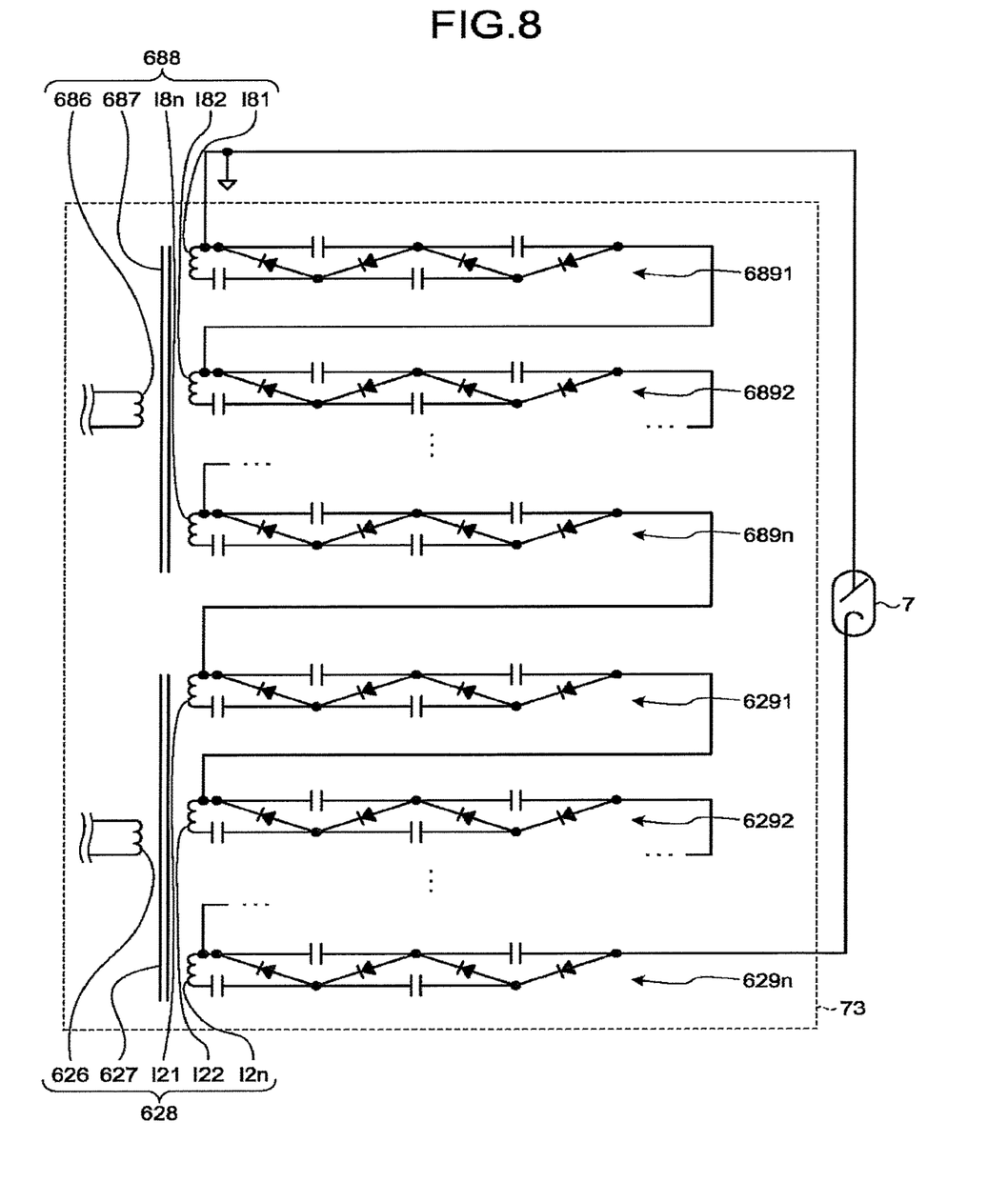
FIG. 8 is a diagram that illustrates an example of the circuit structure of the high-voltage generator of the X-ray high-voltage device according to the embodiment.

FIG. 8 is a circuit diagram that illustrates a high-voltage generator 73 and the X-ray tube 7 in the X-ray high-voltage device for the anode-grounded type X-ray tube. High-voltage rectifying-smoothing circuits 6891 to 689$n$ and the high-voltage rectifying-smoothing circuits 6291 to 629$n$ output a negative direct-current voltage. All of them are cascade-connected, the plus output terminal of the high-voltage rectifying-smoothing circuit 6891 is grounded, and a negative direct-current high voltage is obtained at the minus output terminal of the high-voltage rectifying-smoothing circuit 629$n$. The anode of the X-ray tube 7 is grounded, and a negative direct-current high voltage is applied to its cathode.

As is the case with the circuit in FIG. 7, if the inverter circuits for driving a high-voltage transformer 688 and the high-voltage transformer 628 are operated with a phase shift of 90°, ripple of the voltage applied to the X-ray tube 7 may be reduced. Furthermore, if the polarities of the secondary winding wires of the high-voltage transformer 688 and the high-voltage transformer 628 are alternately reversed, ripple of the voltage applied to the X-ray tube 7 may be further reduced. Here, as illustrated in FIG. 8, the high-voltage transformer 688 includes a primary coil 686, a core 687, and secondary coils l81 to l8$n$.

The X-ray high-voltage device 6 may include one or three or more inverters. The X-ray high-voltage device 6 may supply the alternating current to a primary coil of a single high-voltage transformer by using a single inverter. Alternatively, the X-ray high-voltage device 6 may supply the alternating current to primary coils of high-voltage transformers by using a single inverter.

Next, the advantage of the conductive layer 651 to the conductive layer 65$n$ is explained.

The conductive layer 65$n$ covers all the spaces between the winding wires of the secondary coil l1$n$. Furthermore, the conductive layer 65$n$ is conductive. Therefore, the electric potential of the entire conductive layer 65$n$ has a single value. Thus, all the spaces between the winding wires of the secondary coil l1$n$ do not receive application of the voltage without regard for the environment outside the conductive layer 65$n$. Thus, the conductive layer 65$n$ may prevent damages to the X-ray high-voltage device 6 due to corona discharge that occurs in each space between winding wires of the secondary coil l1$n$. The same holds for the conductive layer 651, the conductive layer 652, or the like.

Furthermore, in the high-voltage generators 71, 72 of the X-ray high-voltage device 6, the conductive layer 651 and the conductive layer 652 to the conductive layer 65$n$ may prevent the occurrence of corona discharge and therefore it is not necessary to fill the space between winding wires of the secondary coil l11 and the secondary coil l12 to the secondary coil l1$n$ with resin. Thus, the manufacturing process of the high-voltage generators 71, 72 in the X-ray high-voltage device 6 is simplified. Furthermore, as the space between winding wires is not filled with resin, the distributed capacitance between winding wires is not increased.

Here, it may be considered that the distributed capacitance is a capacitor that is connected in parallel to each of the secondary coil l11 and the secondary coil l12 to the secondary coil l1$n$. Therefore, the high-voltage generator in the X-ray high-voltage device 6 may prevent an increase in the wattless current. Thus, the X-ray high-voltage device 6 may prevent overheating and efficiency degradation of the inverter.

Furthermore, if the high-voltage transformer, included in the X-ray high-voltage device 6, receives an input of the alternating current, which is close to the resonance frequency, it cannot be used as a normal transformer due to an increase in the impedance. However, as described above, the high-voltage generators 71, 72 in the X-ray high-voltage device 6 may prevent an increase in the distributed capacitance of the secondary coil l11 to the secondary coil l1$n$. Therefore, the X-ray high-voltage device 6 may increase the frequency of the alternating current that is output from the inverter. Furthermore, this allows a reduction in the size of the X-ray high-voltage device 6.

The conductive layer 65$n$ covers the high-voltage rectifying-smoothing circuit 619$n$. Furthermore, the conductive layer 65$n$ is conductive, and it is electrically connected to a single point of the high-voltage rectifying-smoothing circuit 619$n$. For this reason, the electric potential of the entire conductive layer 65$n$ is equal to the electric potential at the single point of the high-voltage rectifying-smoothing circuit 619$n$. Therefore, the conductive layer 65$n$ may prevent damages to the X-ray high-voltage device 6 due to the corona discharge that occurs between the high-voltage rectifying-smoothing circuit 619$n$ and a different component f the X-ray high-voltage device 6. This is because the difference between the maximal value and the minimum value of the voltage, generated by the high-voltage rectifying-smoothing circuit 619$n$, is smaller than the potential difference generated by the corona discharge.

Furthermore, the conductive layer 65$n$ may prevent corona discharge that occurs at corners of electronic components or leads, included in the high-voltage rectifying-smoothing circuit 6191 to the high-voltage rectifying-smoothing circuit 619$n$. Therefore, it is not necessary to process corners of electronic components or leads so as to prevent corona discharge. Furthermore, corona discharge that occurs between the conductive layer 65$n$ and the high-voltage rectifying-smoothing circuit 619$n$ may be prevented by increasing the distance between the conductive layer 65$n$ and the high-voltage rectifying-smoothing circuit 619$n$. The same holds for the conductive layer 651, the conductive layer 652, or the like.

Furthermore, it is preferable that the surfaces of the conductive layer 651 to the conductive layer 65$n$ are curved surfaces or plane surfaces. Specifically, it is preferable that any area on the surfaces of the conductive layer 651 to the conductive layer 65$n$ is a curved surface or a plane surface. This is because, if the conductive layer 651 to the conductive layer 65$n$ have a tapered area or a bent area, there is a possibility that electric field concentration occurs at these areas and corona discharge occurs. Therefore, if the conductive layer 651 to the conductive layer 65$n$ are formed on the outer surfaces of the insulating layer 641 to the insulating layer 64$n$, respectively, it is preferable that the outer surfaces of the insulating layer 641 to the insulating layer 64$n$ are curved surfaces or plane surfaces.

Furthermore, in the high-voltage generators 71, 72 in the X-ray high-voltage device 6, all the secondary coils and the high-voltage rectifying-smoothing circuits, illustrated in FIG. 2, may not be covered with conductive layers. In this case, too, the high-voltage generators 71, 72 in the X-ray high-voltage device 6 may prevent corona discharge that occurs in the space between the winding wires of the secondary coil, covered with the conductive layer, or corona discharge that occurs between the high-voltage rectifying-smoothing circuit, covered with the conductive layer, and a different component of the high-voltage generators 71, 72 in the X-ray high-voltage device 6.

Furthermore, it is preferable that the secondary coil 711 and the high-voltage rectifying-smoothing circuit 6191. The same are covered with a single conductive layer rather than being individually covered with a conductive layer. This is because, if the secondary coil I11 and the high-voltage rectifying-smoothing circuit 6191 are individually covered with a conductive layer, corona discharge sometimes occurs in the conductive wire that connects the secondary coil I11 and the high-voltage rectifying-smoothing circuit 6191. The same holds for the secondary coil I12 and the high-voltage rectifying-smoothing circuit 6192 to the secondary coil I1$n$ and the high-voltage rectifying-smoothing circuit 619$n$, the secondary coil I21 and the high-voltage rectifying-smoothing circuit 6291 and the secondary coil I22 and the high-voltage rectifying-smoothing circuit 6292 to the secondary coil I2$n$ and the high-voltage rectifying-smoothing circuit 629$n$.

Figure 9:
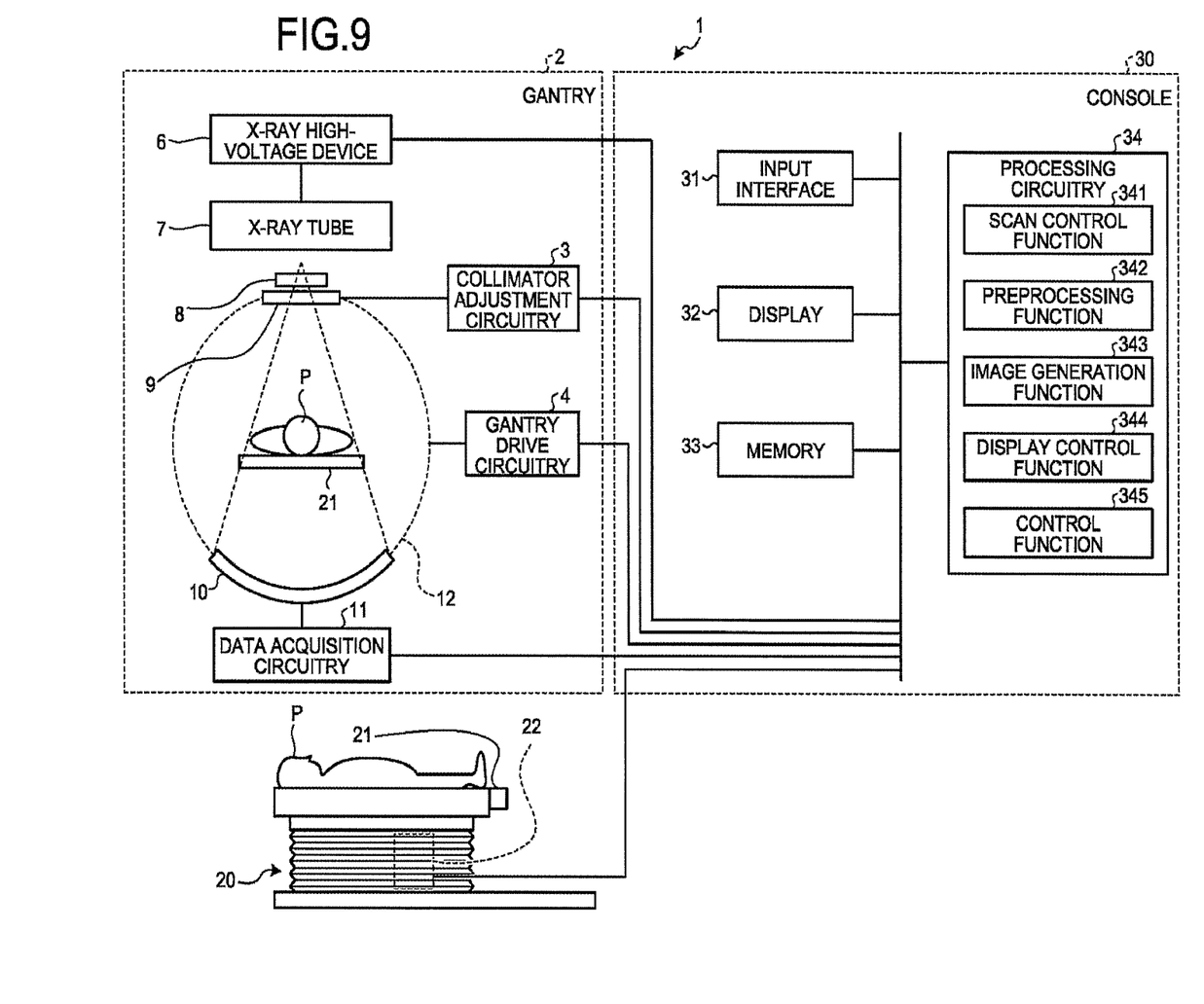
FIG. 9 is a block diagram that illustrates an example of a medical-image diagnostic apparatus that uses the X-ray high-voltage device according to the embodiment.

FIG. 9 is a diagram that illustrates an example of the configuration of a medical-image diagnostic apparatus 1 that uses the X-ray high-voltage device 6 and the high-voltage generators 71, 72 according to the present embodiment. The medical-image diagnostic apparatus 1 is for example an X-ray CT apparatus. As illustrated in FIG. 9, the medical-image diagnostic apparatus 1 includes a gantry 2, a bed 20, and a console 30. Furthermore, the configuration of the medical-image diagnostic apparatus 1 is not limited to the following configuration.

The gantry includes collimator adjustment circuitry 3, gantry drive circuitry 4, the X-ray high-voltage device 6, the X-ray tube 7, a wedge 8, a collimator 9, a detector 10, data acquisition circuitry 11, and a rotary frame 12.

The collimator adjustment circuitry 3 adjusts the aperture and the position of the collimator 9, thereby adjusting the irradiation range of X-rays that are generated by the X-ray tube 7. The collimator adjustment circuitry 3 is connected to the collimator 9, and it includes the mechanism that adjusts the aperture and the position and the circuitry that controls the mechanism. The mechanism includes, for example, a motor and a mechanical element that transmits power, generated by the motor, to the collimator 9. Furthermore, the above-described circuitry includes, for example, circuitry that feeds electric power or control signals to the motor and a processor that controls the circuitry.

The gantry drive circuitry 4 rotates the rotary frame 12, thereby rotating the X-ray high-voltage device 6, the X-ray tube 7, and the detector 10 on the circular orbit with a subject P at the center. The gantry drive circuitry 4 is connected to the rotary frame 12, and it includes a mechanism that rotates it and circuitry that controls the mechanism. The mechanism includes, for example, a motor and a mechanical element that transmits power, generated by the motor, to the rotary frame 12. Furthermore, the above-described circuitry includes, for example, circuitry that feeds electric power or control signals to the motor and a processor that controls the circuitry.

The X-ray high-voltage device 6 generates a high voltage. The X-ray high-voltage device 6 includes the primary coils 616, 626, the secondary coils I11 to I1$n$, and the secondary coils I21 to I2$n$. Furthermore, the X-ray high-voltage device 6 includes the high-voltage rectifying-smoothing circuits 6191 to 619$n$, the high-voltage rectifying-smoothing circuits 6291 to 629$n$, and the conductive layers that cover them. Furthermore, the configurations of them are as described above.

The X-ray tube 7 generates X-rays by using the high voltage that is supplied from the X-ray high-voltage device 6. The X-ray tube 7 includes a cathode, an anode, and a chassis. The cathode emits electrons. The anode receives the electrons and generates X-rays. The chassis houses the cathode and the anode. The inside of the chassis is a vacuum.

The wedge 8 is an X-ray filter that adjusts the dose of radiation and the radiation quality of X-rays that are generated by the X-ray tube 7.

The collimator 9 is a slit for adjusting the irradiation range of X-rays. The collimator 9 is made of material that may shield against X-rays that are generated by the X-ray tube 7. The material is for example lead. The aperture and the position of the collimator 9 are adjusted by the collimator adjustment circuitry 3.

The detector 10 detects X-rays. The detector 10 includes multiple detecting elements. The detector 10 uses the detecting element to detect X-rays that are generated by the X-ray tube 7. The detecting element converts incident X-rays into electric signals and outputs the electric signals to the data acquisition circuitry 11. The size, shape, and number of detecting elements, included in the detector 10, are not particularly limited. Furthermore, the detector 10 may be either a direct-conversion type or an indirect-conversion type. The data acquisition circuitry 11 generates projection data on the basis of electric signals that are output from the detecting element.

The rotary frame 12 is a circular frame. The rotary frame 12 supports the X-ray high-voltage device 6, the X-ray tube 7, and the detector 10. The X-ray tube 7 and the detector 10 are opposed to each other. The rotary frame 12 is driven by the gantry drive circuitry 4 to rotate with the subject P at the center.

The bed 20 includes a top board 21 and bed drive circuitry 22. The top board 21 is a plate-like member on which the subject P is placed. The bed drive circuitry 22 moves the top board 21, on which the subject P is placed, thereby moving the subject P within the capturing hole of the gantry 2.

The console 30 includes an input interface 31, a display 32, a memory 33, and processing circuitry 34.

The input interface 31 is used by a user who inputs commands or settings. The input interface 31 is configured by, for example, a mouse or a keyboard. The input interface 31 transfers commands or settings, input by a user, to the processing circuitry 34. The input interface 31 is implemented by, for example, a processor.

The display 32 is a monitor that is viewed by a user. The display 32 is, for example, a liquid crystal display. The liquid crystal display is a display in which a polarization filter, a glass substrate, a transparent electrode, an oriented film, a liquid crystal layer, a color filter, and a backlight are laminated. The display 32 receives, from the processing circuitry 34, the commands to display for example CT images or the Graphical User Interface (GUI), which is used by a user to input commands or settings. The display 32 presents CT images or the GUI in accordance with the commands.

The memory 33 stores raw data generated by a preprocessing function 342 that is described later, CT images generated by an image generation function 343 that is described later, and programs for the collimator adjustment circuitry 3, the gantry drive circuitry 4, and the data acquisition circuitry 11 to implement the above-described functions. The memory 33 stores a program for the bed drive circuitry 22 to implement the above-described function. The memory 33 stores programs for the processing circuitry 34 to implement a scan control function 341, the preprocessing function 342, the image generation function 343, a display control function 344, a control function 345, described later, and other functions. Therefore, the collimator adjustment circuitry 3, the gantry drive circuitry 4, the data acquisition circuitry 11, the bed drive circuitry 22, and the processing circuitry 34 read and execute programs that are stored in the memory 33, thereby performing the functions.

Furthermore, the memory 33 includes a storage medium that may read stored information by using a computer. The storage medium is, for example, a hard disk.

The processing circuitry 34 includes the scan control function 341, the preprocessing function 342, the image generation function 343, the display control function 344, and the control function 345. The processing circuitry 34 is implemented by, for example, a processor.

The scan control function 341 is a function that controls the medical-image diagnostic apparatus 1 so as perform scanning. The processing circuitry 34 reads the program, which corresponds to the scan control function 341, from the memory 33 and executes it, thereby controlling the medical-image diagnostic apparatus 1 as described below for example.

The processing circuitry 34 controls the bed drive circuitry 22 so as to move the subject P into the capturing hole of the gantry 2. Here, the capturing hole is a hollow that is provided inside the trajectory with which the X-ray tube 7 and the rotary frame 12 rotate. The processing circuitry 34 causes the gantry 2 to perform scanning on the subject P. Specifically, the processing circuitry 34 controls the X-ray high-voltage device 6 so as to supply a high voltage to the X-ray tube 7. The processing circuitry 34 controls the collimator adjustment circuitry 3 so as to adjust the aperture and the position of the collimator 9. Furthermore, the processing circuitry 34 controls the gantry drive circuitry 4 so as to rotate the rotary frame 12. Furthermore, the processing circuitry 34 controls the data acquisition circuitry 11 so as to make the data acquisition circuitry 11 acquire projection data. The scan executed by the medical-image diagnostic apparatus 1 is, for example, conventional scan, helical scan, or step-and-shoot.

The preprocessing function 342 is a function to correct projection data that is generated by the data acquisition circuitry 11. The processing circuitry 34 reads the program, which corresponds to the preprocessing function 342, from the memory 33 and executes it, thereby correcting the projection data. The correction is, for example, logarithmic conversion, offset correction, sensitivity correction, beam hardening correction, or scattered ray correction. The projection data, corrected by the preprocessing function 342, is stored in the memory 33. Furthermore, the projection data, corrected by the preprocessing function 342, is also called raw data.

The image generation function 343 is a function to reconstruct raw data, stored in the memory 33, and generate a CT image. The processing circuitry 34 reads the program, which corresponds to the image generation function 343, from the memory 33 and executes it, thereby generating a CT image. The reconstruction method is, for example, a back projection process or a successive approximation technique. CT images, generated by the image generation function 343, are stored in the memory 33.

The display control function 344 is a function to present CT images, stored in the memory 33, on the display 32. The processing circuitry 34 reads the program, which corresponds to the display control function 344, from the memory 33 and executes it, thereby presenting CT images, stored in the memory 33, on the display 32.

The control function 345 includes a function to operate each component of the gantry 2, the bed 20, and the console 30 at appropriate timing in accordance with a purpose and includes other functions. To perform the above-described process, the processing circuitry 34 reads the program, which corresponds to the control function 345, from the memory 33 and executes it as appropriate.

The medical-image diagnostic apparatus 1 may be an apparatus other than the X-ray CT apparatus. The medical-image diagnostic apparatus 1 may be, for example, an X-ray diagnostic apparatus. The X-ray diagnostic apparatus is, for example, a C-arm type X-ray diagnostic apparatus or an X-ray TV apparatus. The C-arm type X-ray diagnostic apparatus is used for capturing of X-ray fluoroscopic images of a subject. The X-ray TV apparatus is used for, for example, gastrointestinal tract contrast examination, urinary tract contrast examination, spinal cord cavity contrast examination, or biliary tract contrast examination.

The above-described processor is, for example, a central processing unit. (CPU), a graphics processing unit (GPU), an application specific integrated circuit (ASIC), a programmable logic device (PLD), or a field programmable gate array (FPGA). Furthermore, the programmable logic device (PLD) is, for example, a simple programmable logic device (SPLD) or a complex programmable logic device (CPLD).

According to the above-described embodiment, the collimator adjustment circuitry 3, the gantry drive circuitry 4, the data acquisition circuitry 11, the bed drive circuitry 2, and the processing circuitry 34 read programs, stored in the memory 33, and execute them to implement their functions; however, this is not a limitation. Instead of storing programs in the memory 33, a program may be directly installed in each of the circuitry. In this case, the circuitry reads the directly installed programs and execute them to implement their functions.

The circuits, illustrated in FIG. 9, may be separated or combined as appropriate. For example, the processing circuitry 34 may be separated into scan control circuitry, preprocessing circuitry, image generation circuitry, display control circuitry, and control circuitry that implement functions, such as the scan control function 341, the preprocessing function 342, the image generation function 343, the display control function 344, and the control function 345. Furthermore, for example, the collimator adjustment circuitry 3, the gantry drive circuitry 4, the data acquisition circuitry 11, the bed drive circuitry 22, and the processing circuitry 34 may be combined optionally.

According to at least one of the above-described embodiments, it is possible to provide a medical-image diagnostic apparatus and an X-ray high-voltage device, with which corona discharge may be prevented.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A high-voltage device comprising:
an inverter circuit configured to convert a direct-current voltage into an alternating-current voltage;

a high-voltage transformer including a primary coil on an input side and multiple secondary coils on an output side and raising a voltage of an output of the inverter circuit;

a high-voltage rectifying-smoothing circuit configured to rectify an output of the high-voltage transformer;

an insulating layer provided on an outer circumference of a bundle of winding wires of each of the secondary coils so as to individually cover each of the secondary coils and to further cover the high-voltage rectifying-smoothing circuit in addition to the secondary coil; and a conductive layer provided on an outer circumference of each of the insulating layers so as to individually cover each of the insulating layers, wherein the conductive layer is provided on circumferences of both the secondary coil and the high-voltage rectifying-smoothing circuit with the insulating layer interposed.

2. The high-voltage device according to claim 1, wherein the insulating layer is a container made of insulating material to house at least one of the secondary coil and the high-voltage rectifying-smoothing circuit.

3. The high-voltage device according to claim 1, wherein the conductive layer covers an entire surface of the high-voltage rectifying-smoothing circuit and electrically connects to a single point of the high-voltage rectifying-smoothing circuit.

4. The high-voltage device according to claim 3, wherein the conductive layer is electrically connected to an input terminal of the high-voltage rectifying-smoothing circuit.

5. The high-voltage device according to claim 3, wherein the conductive layer is electrically connected to an output terminal of the high-voltage rectifying-smoothing circuit.

6. The high-voltage device according to claim 1, wherein an outer surface of the insulating layer is a curved surface or a plane surface, and the conductive layer is formed on the outer surface of the insulating layer.

7. A medical-image diagnostic apparatus comprising:
a high-voltage device generating a high voltage; and
an X-ray tube generating an X-ray by using the high voltage supplied from the high-voltage device, wherein the high-voltage device comprises an inverter circuit converting a direct-current voltage into an alternating-current voltage;

a high-voltage transformer including a primary coil on an input side and multiple secondary coils on an output side and raising a voltage of an output of the inverter circuit;

a high-voltage rectifying-smoothing circuit configured to rectify an output of the high-voltage transformer;

an insulating layer provided on an outer circumference of a bundle of winding wires of each of the secondary coils so as to individually cover each of the secondary coils and to further cover the high-voltage rectifying-smoothing circuit in addition to the secondary coil; and a conductive layer provided on an outer circumference of each of the insulating layers so as to individually cover each of the insulating layers, wherein the conductive layer is provided on circumferences of both the secondary coil and the high-voltage rectifying-smoothing circuit with the insulating layer interposed.

8. The high-voltage device according to claim 1, wherein the inverter circuit includes switching elements which convert the direct-current voltage to into the alternating-current voltage.

9. The high-voltage device according to claim 1, wherein the conductive layer individually covers substantially a whole surface of each of the insulating layers.

* * * * *